(12) United States Patent
Letcher (10) Patent No.: US 7,758,346 B1
(45) Date of Patent: Jul. 20, 2010

(54) IMPLANT PROSTHODONTICS AND METHODS OF PREPARING AND SEATING THE SAME

(76) Inventor: William F. Letcher, 5522 S. Lewis Ave., Tulsa, OK (US) 74105

(*) Notice: Subject to any disclaimer, the term of this patent is extended or adjusted under 35 U.S.C. 154(b) by 465 days.

(21) Appl. No.: 11/734,138

(22) Filed: Apr. 11, 2007

Related U.S. Application Data (60) Provisional application No. 60/863,232, filed on Oct. 27, 2006.

(51) Int. Cl.
*A61C 9/00* (2006.01)
(52) U.S. Cl. .................. 433/214; 433/172; 433/213
(58) Field of Classification Search ............ 433/167, 433/172, 173, 176, 199.1, 213, 214, 218–220, 433/223, 229; 264/17
See application file for complete search history.

(56) References Cited

U.S. PATENT DOCUMENTS

| | | | |
|---|---|---|---|
| 2,662,288 A * | 12/1953 | McNally ................. 433/184 |
| 3,748,739 A | 7/1973 | Thibert |
| 3,905,108 A | 9/1975 | Weiss et al. |
| 3,921,292 A | 11/1975 | Iychenko |
| 4,094,067 A * | 6/1978 | Hazar ..................... 433/213 |
| 4,290,755 A * | 9/1981 | Scott ...................... 433/173 |
| 4,543,063 A | 9/1985 | Cohen |
| 4,654,006 A * | 3/1987 | Kusano et al. ........... 433/168.1 |
| 4,787,851 A * | 11/1988 | Kusano et al. ............ 433/173 |
| 4,906,420 A | 3/1990 | Brajnovic et al. |
| 5,064,374 A | 11/1991 | Lundgren |
| 5,171,147 A | 12/1992 | Burgess |
| 5,413,480 A | 5/1995 | Musikant et al. |
| 5,427,906 A * | 6/1995 | Hansen .................... 433/173 |
| 5,554,665 A | 9/1996 | Tateosian et al. |
| 5,678,997 A * | 10/1997 | De Buck ................. 433/177 |
| 5,716,214 A | 2/1998 | Lund et al. |
| 5,749,732 A | 5/1998 | Sendax |
| 5,775,900 A | 7/1998 | Ginsburg et al. |
| 5,856,374 A | 1/1999 | Ono et al. |
| 5,876,209 A | 3/1999 | Letcher |
| 5,877,232 A | 3/1999 | Storch et al. |
| 5,885,077 A | 3/1999 | Jeffer |
| 5,885,078 A | 3/1999 | Cagna et al. |
| 5,971,760 A | 10/1999 | Letcher |
| 5,977,199 A | 11/1999 | Xie |
| 6,048,203 A * | 4/2000 | Rosenberg ............... 433/173 |
| 6,056,547 A * | 5/2000 | Names .................... 433/173 |
| 6,114,409 A | 9/2000 | Krebber |
| 6,116,070 A * | 9/2000 | Oshida et al. ............. 72/60 |
| 6,200,136 B1 | 3/2001 | Prasad et al. |
| 6,322,364 B1 | 11/2001 | Oshida et al. |
| 6,506,052 B1 * | 1/2003 | Hoffman ................. 433/181 |
| 6,849,670 B2 | 2/2005 | Satoh et al. |
| 6,872,076 B2 | 3/2005 | Karmaker et al. |

(Continued)

*Primary Examiner*—Cris L Rodriguez
*Assistant Examiner*—Michael R Ballinger
(74) *Attorney, Agent, or Firm*—Head, Johnson & Kachigian, P.C.

(57) ABSTRACT

Novel prosthetic teeth constructed using moldable, microfilled composite resin, and a novel method for making and bonding the same onto implants in a patient's mouth. The teeth are prepared and seated in the patient's mouth using materials and methods that are known and widely available. The present invention may be applied to any situation in which one or more replacement teeth are required, including full-arch replacement for upper and/or lower teeth.

34 Claims, 9 Drawing Sheets

U.S. PATENT DOCUMENTS

| | | |
|---|---|---|
| 6,933,327 B2 | 8/2005 | Yamakawa et al. |
| 7,108,511 B1 | 9/2006 | Shatkin |
| 7,234,940 B2 | 6/2007 | Weissman |
| 7,322,824 B2 | 1/2008 | Schmitt |
| 7,431,589 B2 * | 10/2008 | Weissman .................. 433/174 |
| 2003/0039943 A1 | 2/2003 | Worthington |
| 2003/0183964 A1 | 10/2003 | Daskalon et al. |
| 2004/0048949 A1 | 3/2004 | Rudo |
| 2004/0058299 A1 | 3/2004 | Molin et al. |
| 2004/0166304 A1 | 8/2004 | Vallittu et al. |
| 2005/0032024 A1 | 2/2005 | Catellon et al. |
| 2005/0214717 A1 | 9/2005 | Freilich et al. |
| 2006/0204931 A1 | 9/2006 | Ibsen et al. |
| 2006/0269902 A1 * | 11/2006 | Weissman .................. 433/173 |
| 2007/0190488 A1 | 8/2007 | Rusler |
| 2007/0224576 A1 | 9/2007 | Ihde et al. |

* cited by examiner

IMPLANT PROSTHODONTICS AND METHODS OF PREPARING AND SEATING THE SAME

CROSS-REFERENCE

This application claims the benefit of U.S. Provisional Application No. 60/863,232, filed Oct. 27, 2006, which is herein incorporated by reference.

STATEMENT REGARDING FEDERALLY SPONSORED RESEARCH OR DEVELOPMENT

Not Applicable.

REFERENCE TO A SEQUENCE LISTING, A TABLE, OR A COMPUTER PROGRAM LISTING COMPACT DISC APPENDIX

Not Applicable.

BACKGROUND OF THE INVENTION

For persons who have lost an appreciable number of their natural teeth, whether due to disease, decay or other natural or unnatural processes, there is likely to be significant social withdrawal, shame, humiliation and a corresponding loss of dignity. While prosthodontic medicine has greatly enhanced the quality of life of such persons artificial or prosthetic teeth, there remains room for improvement. Traditional dentures, for example, have evolved and undergone substantial improvement in appearance as well as function. However, persons wearing traditional dentures still face a number of problems, including progressive bone loss, inadequate adhesion, poor fit, slippage, unwanted Movement, general discomfort, adverse psychological effects, infiltration of food particles, and maintenance. Prosthetic teeth for use with implants and a novel method for making and using the same are described herein, thus enabling dentists to provide patients with a long-term, durable, fixed-bridge alternative that can be achieved with minimal disruption or inconvenience.

BRIEF SUMMARY OF THE INVENTION

Described herein are novel prosthetic teeth constructed using moldable, micro-filled composite resin, and a novel method for making and seating the same onto appliances surgically implanted in a patient's mouth. The teeth, which are both functionally and aesthetically superior to prior art prosthodontia, are prepared and placed using a number of materials and methods that are known and widely available. The present invention may be applied to any situation in which one or more replacement teeth are required, including full-arch replacement for upper and/or lower teeth.

While micro-filled composite resin has long been recognized as a useful tooth filling material for anterior or posterior restorations, it has not yet found its way into implant prosthodontic applications such as full bridges and dentures. The benefits of resin over prior art materials such as acrylics, ceramics and porcelain are numerous. Chief among them is the ability of the dentist to work, shape and re-shape the teeth for aesthetic as well as functional reasons. Additional resin may be added to the teeth, and the teeth may be readily re-shaped using myriad filing and drilling techniques.

Unlike prosthetic teeth made from porcelain, it is never too late to add or remove material; resin teeth are amenable to such modifications even after fully cured and even after the new teeth are in place. This enables the practitioner to make a number of adjustments to accommodate unforeseen or unexpected situations that simply cannot be anticipated through the use of cast molds in the laboratory. Aesthetically speaking, resin is available in a number of color variants.

Resin is light-cured, and such curing can typically take place in a manner of minutes using visible light, as opposed to oven-baking porcelain or using high-intensity ultraviolet light on ceramic.

Resin is noteworthy for its strength as much as its versatility. Furthermore, bonding the resin directly to the patient's surgical implants is preferable over O-rings, cements, screws or other mounting methods previously employed. The problems patients experience with slippage and unwanted movement, however slight, are eliminated.

The instant invention is also advantageous in that a patient can have the prosthetic teeth cast, prepared and inserted during the same post-operative office visit. Because the materials and methods are all readily available and accessible to practicing dentists, the cost and inconvenience of having to send molds to a third-party, offsite laboratory is eliminated. This maximizes efficiency and minimizes the disruption to the patient, such as having to make multiple return trips to the provider.

DETAILED DESCRIPTION OF THE INVENTION

The embodiments discussed herein are merely illustrative of specific manners in which to make and use the invention and are not to be interpreted as limiting the scope of the instant invention.

While the invention has been described with a certain degree of particularity, it is to be noted that many modifications may be made in the details of the invention's composition and the arrangement of its components without departing from the spirit and scope of this disclosure. It is understood that the invention is not limited to the embodiments set forth herein for purposes of exemplification.

Notwithstanding the exemplary embodiments set forth below, the prosthetic teeth and methods described herein should not be interpreted as being limited to a certain class or classes of patients. Prosthodontic patients naturally come to dentists with infinitely diverse treatment histories. Moreover, presenting dentition will necessarily and widely vary.

For example, some candidates for prosthodontic treatment will have already lost all of their natural teeth and have been fitted or supplied with full prosthetics. Such prosthetics could include bridges, implants or dentures. Some patients will have one or more healthy natural teeth remaining and may only have partial prosthetics. Still others may require that one or more diseased or malpositioned teeth are extracted before prosthodontic treatment may proceed. Some natural teeth may be reduced or prepared to receive a prosthetic, but not extracted. Depending on the circumstances, a patient might require a full upper arch but not a lower arch, or vice versa.

Persons skilled in the art will appreciate that the procedures for upper and lower arches and bridges are essentially the same.

As with any dental or prosthodontic procedure, contraindications for treatment are determined in the professional judgment of the practitioner.

The process begins with the preparation in the usual manner of an initial impression of the patient's upper and/or lower mouth without any removable prosthetics in place. For example, in an edentulous patient with a removable full denture, this impression will be of the patient's gum line. Whereas, for patients with healthy partial dentition and/or acceptable partial appliances, who are to be provided with less than a full arch of teeth, this impression will faithfully replicate the gaps or spaces to be addressed. Insofar as this disclosure generally contemplates an edentulous patient, no restrictions on the procedure are to be inferred therefrom.

If the practitioner, upon identifying and assessing the patient's existing dentition and appliances (e.g., implants), thereafter determines in his or her professional judgment that one or more natural teeth require extraction or reduction, such teeth may be extracted or reduced utilizing common, accepted techniques in the art. For example, one or more teeth may be extracted in an office setting under local anesthesia. A new impression would then be prepared.

Figure 1:
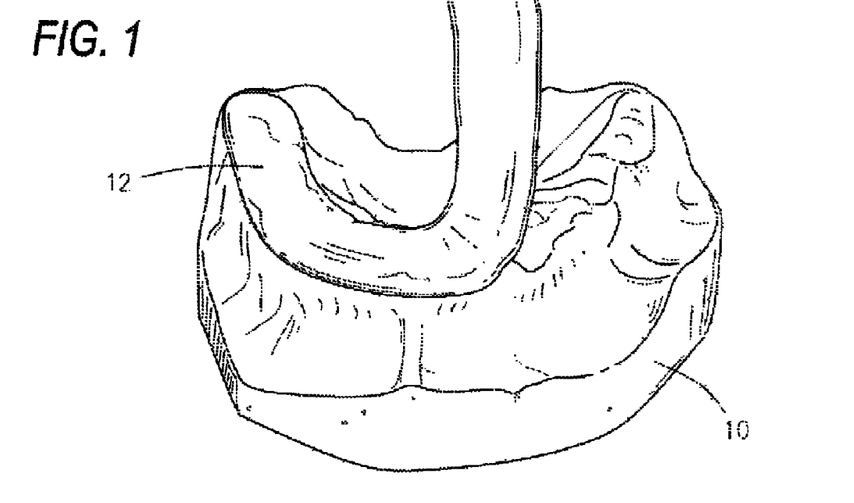
FIGS. 1-14 each illustrate one or more steps of the method disclosed in the present invention as well as the apparatus thereby produced.
Figure 2:
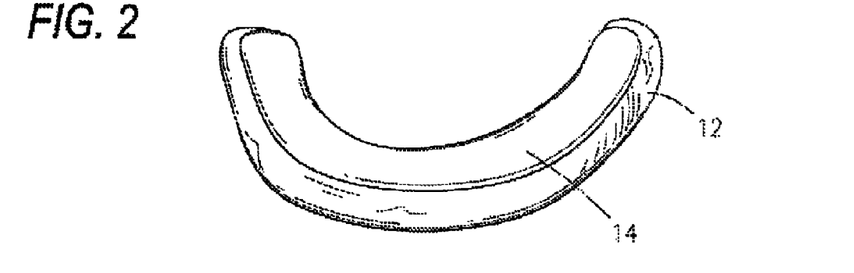

The impression is poured up in dental stone and allowed to harden, forming an initial model 10. (See FIG. 1) A shellac baseplate 12 is molded onto the gum line of initial model 10. Turning to FIG. 2, pink baseplate wax 14 is added to baseplate 12. Baseplate 12 is inserted into the patient's mouth and the wax 14 is formed to approximate the proper length and position of any one or more teeth which are missing from the patient's mouth. Wax 14 is also formed to imitate the support typically provided by natural dentition to the patient's lips. Skilled practitioners can appreciate that the use of a baseplate is not necessary for a single tooth application or where there are sufficient remaining teeth for bite registration and teeth positioning. Baseplates are increasingly helpful as the number of missing teeth increases.

A separate sample of wax (hereinafter, bite registration wax) is then used to capture the centric bite registration of the patient by establishing the 'vertical and centric' of the patient using a face-bow and techniques that are well known in the art.

Figure 3:
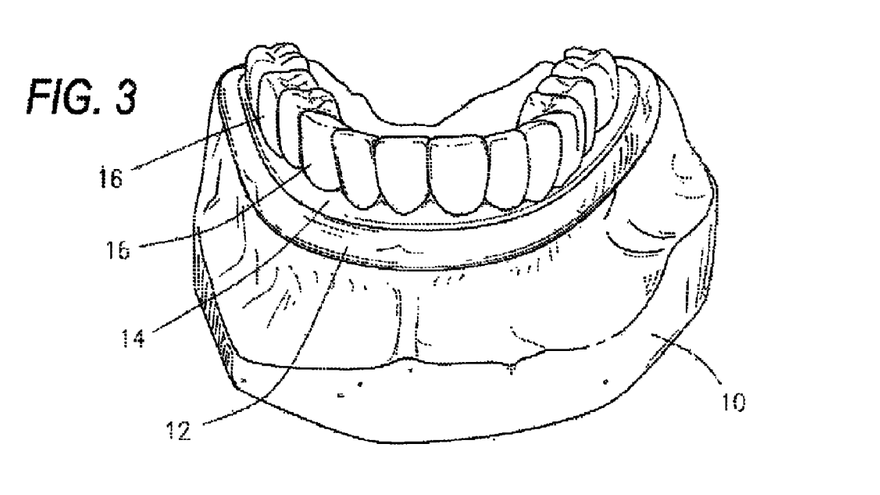

With respect to FIG. 3, initial model 10 is properly mounted on an articulator (not shown), with the aid of the bite registration wax and baseplate 12. A denture setup is then prepared, using techniques that are well known in the art. As disclosed herein, one or more reference teeth 16 are selected to aesthetically compliment the patient's face, paying particular attention to shape. For example, patients with round faces are generally provided 'round ovoid' teeth, while persons having rectangular faces receive 'square tapering' teeth. Tooth shape kits are helpful in this regard. Reference teeth 16 are fitted to baseplate 12 using the molded wax 14 as a guide. As an alternative to selecting teeth when a full arch is required, pre-formed full arches may be utilized. Reference teeth 16 and baseplate 12 are placed in the patient's mouth to confirm the desired aesthetics and in order to validate the previous bite registration.

Pre-existing prosthetics such as dentures can be utilized as a model, but are often inadequate due to excessive wear, in addition to various aesthetic deficiencies such as improper shape and position.

Figure 4:
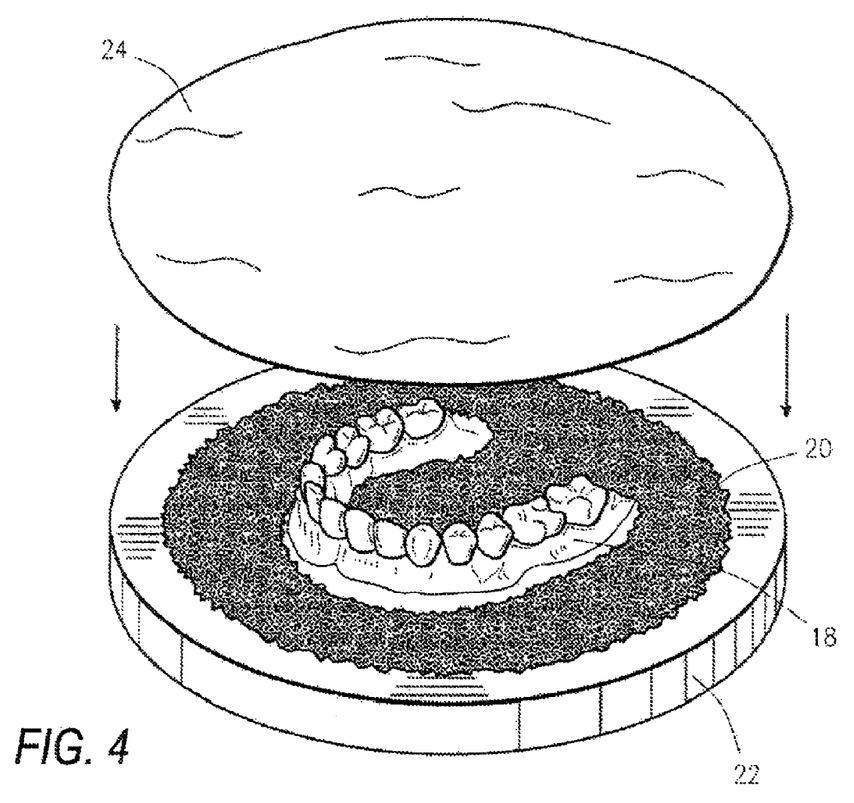

Reference teeth 16 and baseplate 12 are returned to initial model 10 on the articulator and all excess shellac and wax (i.e., other than what is required to hold reference teeth 16 in the proper position) is removed. An exact copy of the denture setup (comprising reference teeth 16 on initial model 10) is made with impression material and poured up in dental stone, thereby forming second model 18 (See FIG. 4).

Figure 5:
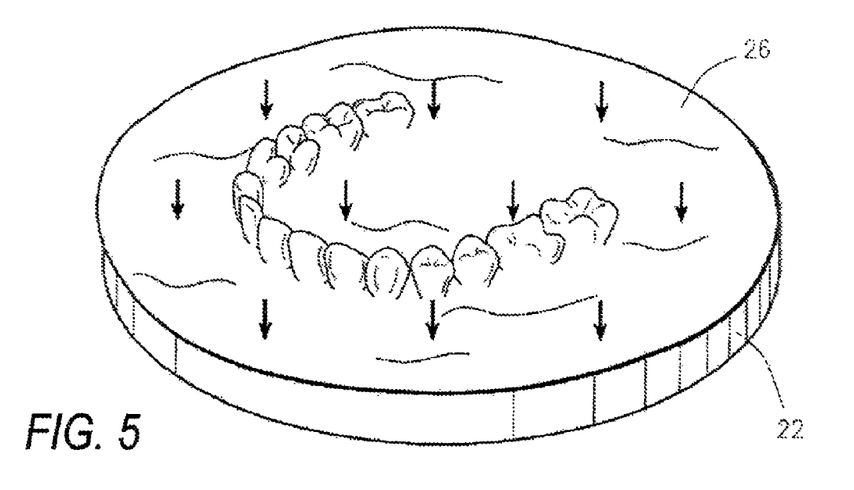

A mold of second model 18 is then prepared. This mold can be prepared in a number of ways, but must be adapted to receive a moldable, dental restorative material. Furthermore, the mold must not interfere with or impede the curing of said material. In the disclosed embodiment, the mold is prepared in the following manner. Still referring to FIG. 4, second model 18 is placed on a bed of granular material 20 resting on platform 22 of a positive pressure device such as the Biostar™ (SCHEU-DENTAL, Germany; distributed by GREAT LAKES ORTHODONTICS, LTD., Tonawanda, N.Y.) (not shown) and overlaid under heat and pressure with a single sheet of clear, 1.0 mm Copyplast™ film 24 (SCHEU-DENTAL, Germany), thereby forming Copyplast™ mold 26 (See FIG. 5). Persons skilled in the art will appreciate that heat, pressure and time settings for the Biostar™ and Copyplast™ film should be consistent with the manufacturer's instructions for each.

The practitioner determines if the patient's reduced natural teeth and/or appliances are sufficient in quantity and quality to support a long-term provisional prosthesis. If the patient is edentulous or, in the judgment of the practitioner, additional implants are desired, surgical implantation is then performed as set forth generally herein.

Figure 6:
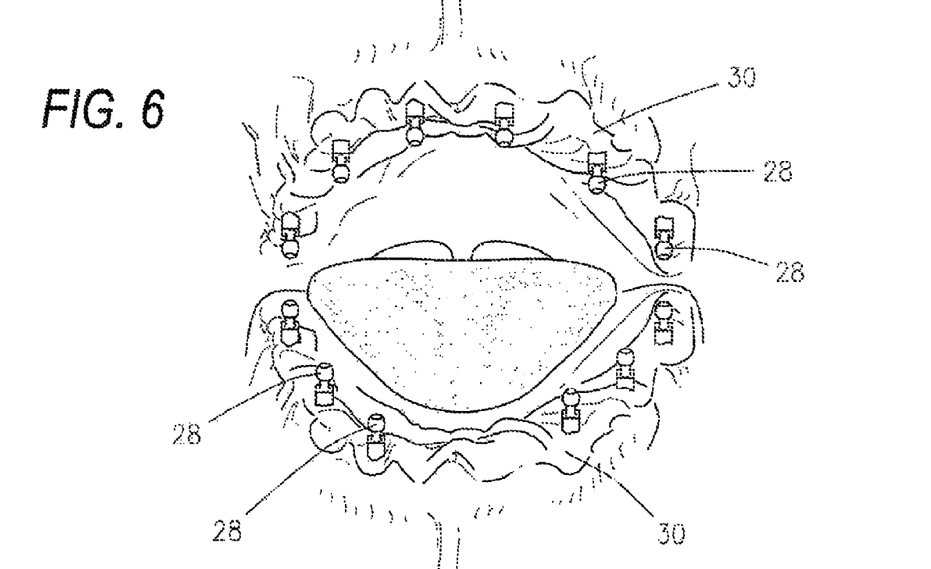

Turning to FIG. 6, a sufficient number of implants 28, such as MDL™ mini-implants (TM applied for, INTRA-LOCK INTERNATIONAL, INC., Boca Raton, Fla.) are surgically placed through the patient's gum line 30 and into the patient's jaw using appropriate surgical techniques. The number of mini-implants will vary. Preferably, where the patient is edentulous and has no prior implants, a total of 8 to 12 mini-implants will be placed for full upper and lower replacement. Mini-implants are generally constructed of titanium alloy and are generally from 2.0-2.5 mm in diameter. Alternatively, traditional dental implants may be used.

Successful planning and placement of the mini-implants may be aided and verified with traditional radiographic (X-rays) as well as computed tomography (CT) information. Of particular importance are bone depth, size and shape of the maxillary sinuses, and the location of nerves associated with the mandibular branch of the trigeminal nerve (inferior alveolar nerve). Panoramic X-rays show two dimensions (width and breadth), but the images are somewhat distorted. CT scanning offers the additional benefits of depth, three-dimension images, and no distortion. Implant selection and placement aided by CT is accordingly more precise.

Mini-implants may pierce the sinus floor without complication. Persons skilled in the art will appreciate that sinus elevation may be performed in certain cases. In such cases, the placement of implants will generally be delayed from six to nine months.

Figure 7:
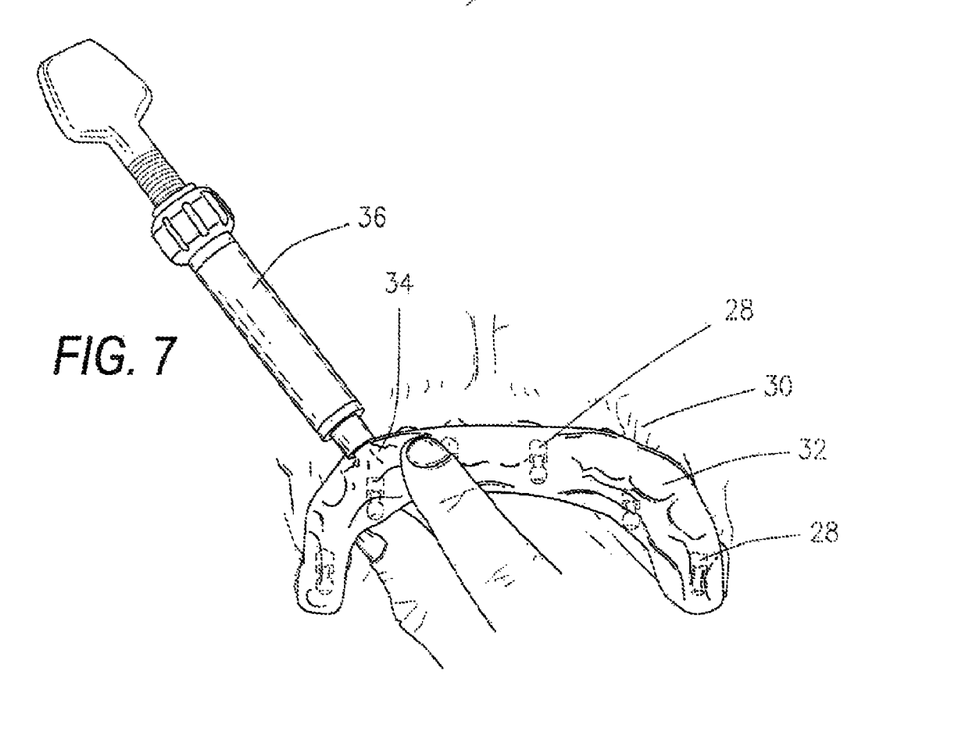

With respect to FIG. 7, a continuous meso-ridge structure 32 is built in the mouth along the patient's gum line using an appropriate, moldable dental restorative material 34 such as Estelite® (TOKUYAMA CORP., Japan). Material 34 may be dispensed from a suitable dispenser 36, typically using the syringe provided by the manufacturer. The meso-ridge is typically built manually, but one or more appliances or tools could be utilized for molding, shaping, etc.

Estelite®, a micro-filled, light curable composite resin, is selected for demonstrative purposes herein, but persons skilled in the art will appreciate that any moldable dental restorative material may be used. This includes composite resins as well as acrylics. Composite resins, as used herein, include hybrid composites, nanohybrid composites, microfilled composites and flowable composites. It will be appreciated that other suitable materials, such as resin/glass ionomers, sculptable compomers and core buildup materials could also be utilized. The only requirements are that the material be moldable and be either self-curing or curable using means readily available in the laboratory such as heat and light.

Figure 8:
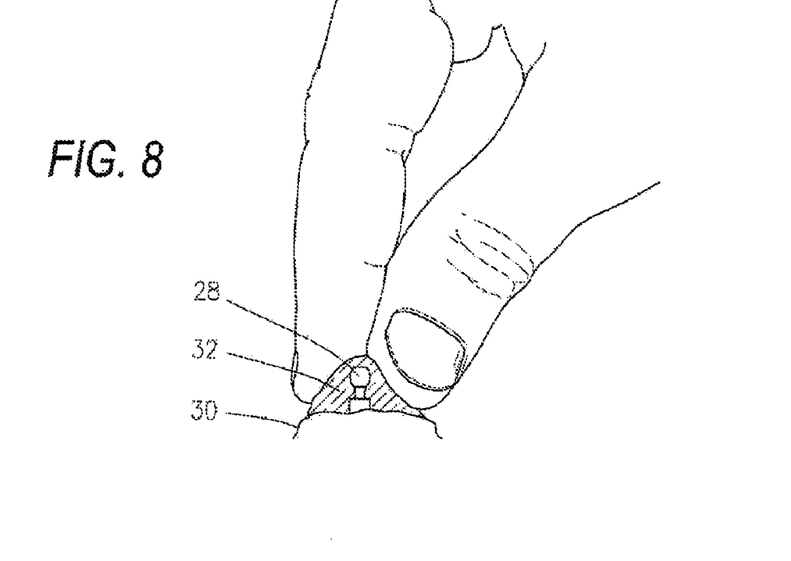
Figure 9:
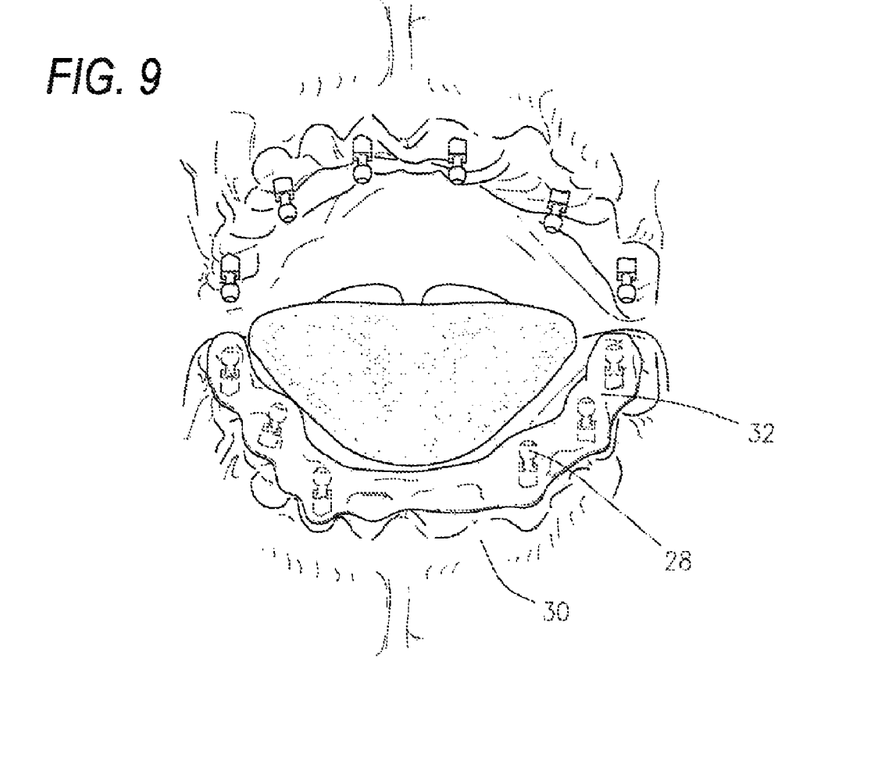

Meso-ridge 32 effectively connects and conceals implants 28, forming a single, unitary structure in the mouth where the prosthesis is desired. FIG. 8 is a cross-section depicting the erection of meso-ridge 32 about implants 28 and along the patient's gum line 30. As shown in FIG. 9, where implants 28 and/or reduced natural teeth are not situated in parallel about the patient's gum line 30, the meso-ridge 32 may be constructed in a serpentine fashion or with undulations so as to track their course and ensure a continuous, unitary structure.

The meso-ridge is subjected to an external light source (not shown), preferably a handheld LED curing light in the blue visible spectrum (about 430 to 490 nm) and cured. The cure time will vary depending on the light source. In the preferred embodiment, it takes approximately 10 seconds to cure a 6 mm thickness of resin. Other curing light sources may take anywhere from 4-40 seconds to cure the same thickness. It should also be appreciated that depending on the material selected, meso-ridge 32 may be self-curing or curable using other readily available means such as external heat.

Figure 10:
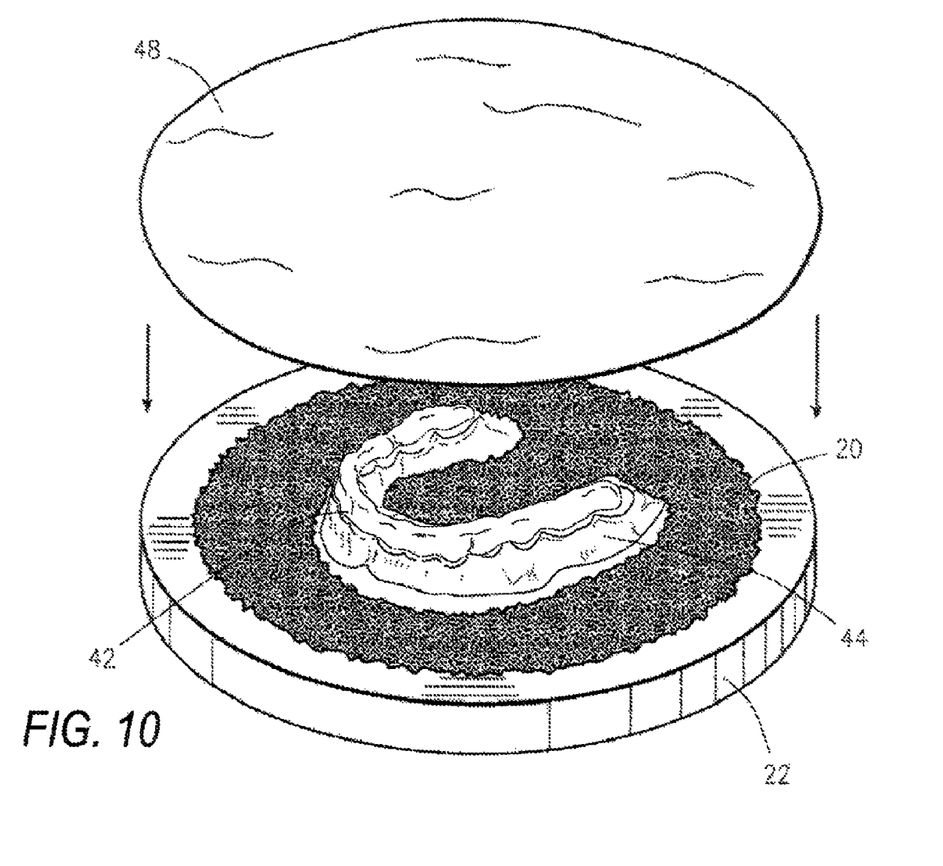

A faithful impression of the patient's mouth—including the cured meso-ridge—is taken and poured up in dental stone using common techniques, thereby forming third model 44 (See FIG. 10). Third model 44 features a ridge 42 which corresponds to and replicates the meso-ridge built in the patient's mouth.

Figure 11:
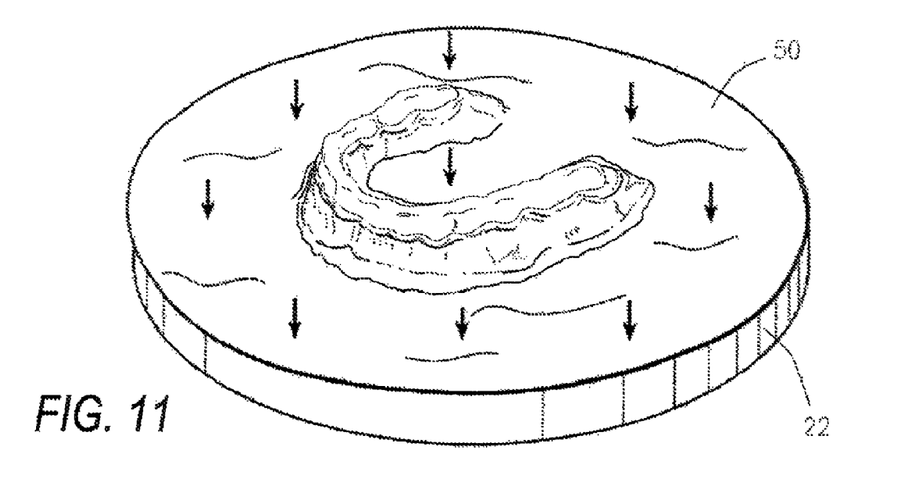

Third model 44 is then placed into the Biostar™ (not shown) and overlaid under heat and pressure with a single sheet of 0.1 mm Isofolan™ film 48 (SCHEU-DENTAL, Germany), thereby forming Isofolan™ mold 50 (See FIGS. 10 and 11). Persons skilled in the art will appreciate that heat, pressure and time settings for the Biostar™ and Isofolan™ films should be consistent with the manufacturer's instructions for each. Isofolan™ mold 50 includes Isofolan™ film 48 and third model 44 which is retained thereunder. The Isofolan™ film 48 facilitates the removal of materials, such as new prosthetic teeth, to be fabricated from third model 44. As such, the use of Isofolan™ is optional. Excess Isofolan™ film 48 may be trimmed from mold 50.

Figure 12:
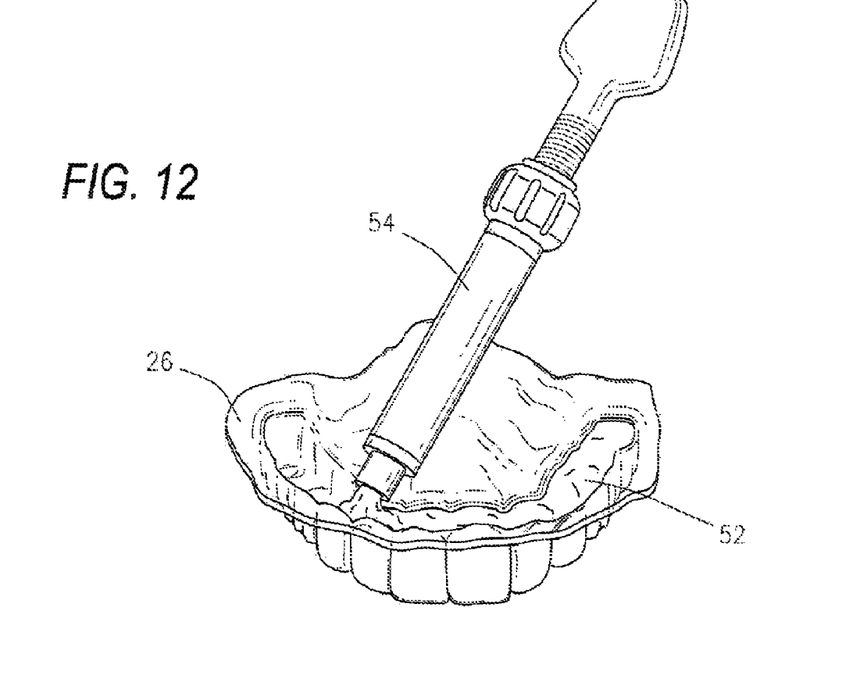

Turning now to FIG. 12, Copyplast™ mold 26 is filled with a moldable, dental restorative material 52 such as the microfilled, light-curable composite resin Estelite®. Material 52 is dispensed from a suitable dispenser 54, typically using the syringe provided by the manufacturer. The prosthetic teeth can be prepared using the same substance as the meso-ridge (e.g., Estelite® as disclosed herein), but there is no such requirement. The selection criteria for material 52 is the same as described above for material 34.

Figure 13:
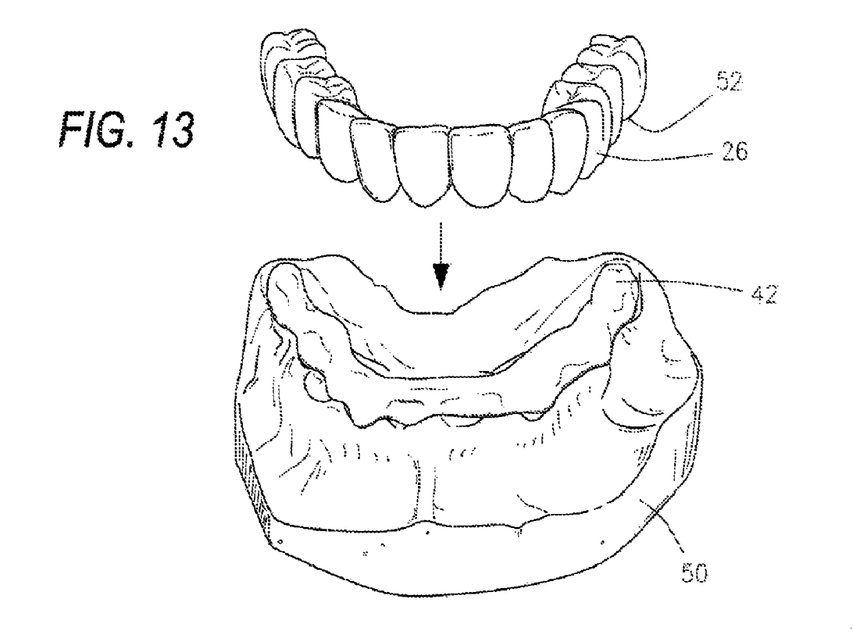
Figure 14:
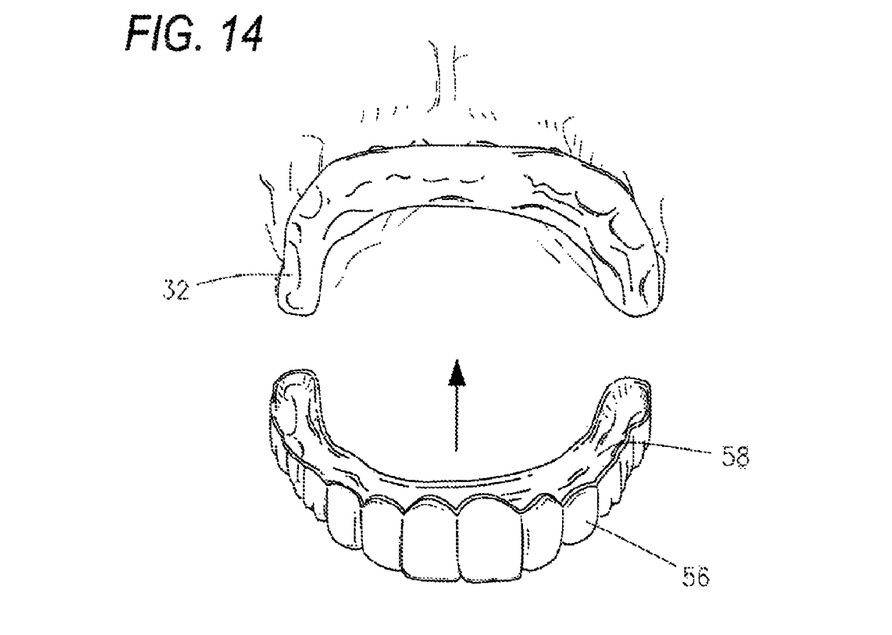

Copyplast™ mold 26 filled with material 52 is placed directly onto Isofolan™ mold 50 (See FIG. 13) and subjected to an external light source (not shown) and cured in the same manner as meso-ridge 32 above, thereby forming prosthetic teeth 56 (see FIG. 14). It should again be appreciated that depending on the material selected, prosthetic teeth 56 may be self-curing or curable using other readily available means such as external heat.

Copyplast™ mold 26 containing cured prosthetic teeth 56 is removed from Isofolan™ mold 50. Isofolan™ film 48 from mold 50 may adhere to the intaglio or gum surface of prosthetic teeth 56 when Copyplast™ mold 26 is removed, but film 48 need simply be pulled away to expose prosthetic teeth 56. Prosthetic teeth 56 are then removed from Copyplast™ mold 26.

It will be appreciated that the intaglio surface of prosthetic teeth 56 will have a recess 58 that corresponds with ridge 42 on Isofolan™ mold 50 and, consequently, with the meso-ridge 32 constructed in the patient's mouth. This, of course, facilitates the placement of prosthetic teeth 56 in patient.

Prosthetic teeth 56 may be refined, shaped and polished using dental laboratory tools and standard dental or prosthodontic techniques for both aesthetic (e.g., tooth shape, separation and definition) and functional (e.g., bite refinements, removing excess bulk to ensure patient comfort) purposes.

During the seating process (FIG. 14), meso-ridge 32 may be cleaned, and the intaglio or gum surface 58 of prosthetic teeth 56 may be coated with a suitable bonding agent (not shown). Fresh material 52 (not shown in FIG. 14) is applied to intaglio surface 58. Prosthetic teeth 56 are placed in the patient's mouth and pressed onto meso-ridge 32. Excess resin is removed by scraping with an appropriate tool; gaps or spaces may be filled with fresh material 52. The material is light cured as described above. This solidly fixes the prosthetic teeth 56 to meso-ridge 32.

Alternatively, in lieu of a meso-ridge, the prosthetic teeth may be seated directly upon a patient's implants as follows. Using materials and techniques that are well known in the art, the patient's Copyplast™ mold is utilized to prepare temporary teeth constructed with methyl-methylacrylate ("acrylic"). Practitioners will recognize that acrylic is self-curing and that such curing takes place in about live minutes. Other moldable, dental restorative materials could be used.

Figure 15:
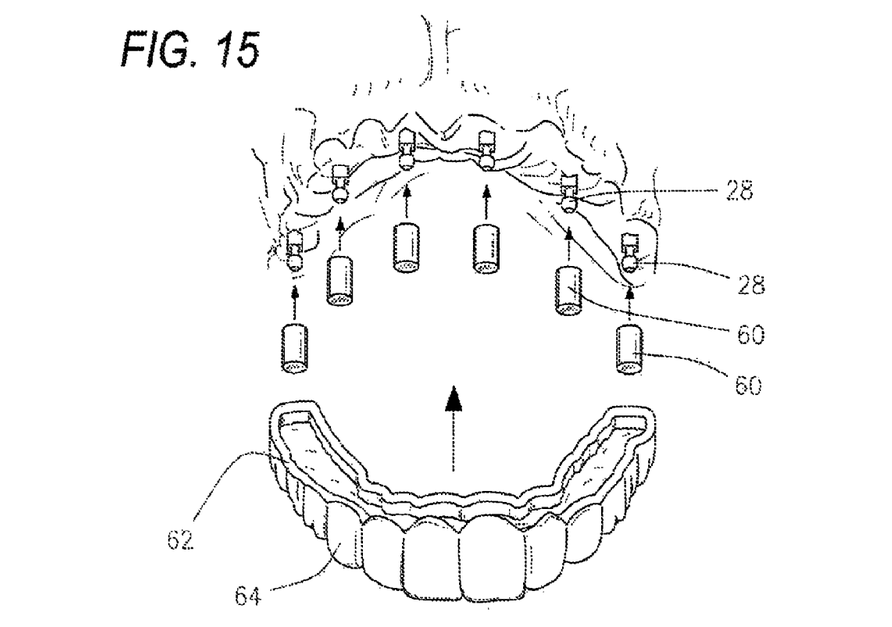
FIGS. 15-19 each represent additional, intermediate steps performed in an alternative embodiment of the invention disclosed herein.

Turning to FIG. 15, O-ring housings 60, each containing an O-ring (not shown), are placed on the patient's implants 28. With respect to FIG. 15, the gum side 62 of temporary teeth 64 is hollowed out and adapted to receive the O-ring housings 66. Fresh acrylic is added to the hollowed-out portion of temporary teeth 64, which are then seated in place on the O-ring housings 60 in patient's mouth and allowed to cure. Upon curing, temporary teeth 64 incorporate O-ring housings 60 and O-rings, and may be removed from the mouth. Excess acrylic may simply be trimmed away. Temporary teeth 64 fit frictionally and securely about the mini-implants 28 in the patient's mouth by way of the O-rings. It should be appreciated that acrylic temporary teeth 64 would be suitable for use by the patient immediately after implant surgery and could remain in place throughout post-operative healing.

If necessary, adjustments may be made to the patient's acrylic temporary teeth. Once the patient is satisfied with the look, feel and function of the temporaries, a face-bow transfer recording is prepared using methods that are well known in the art (not illustrated). A wax bite registration is made between the patient's upper and lower teeth (not illustrated). Practitioners skilled in the art will appreciate that these steps will help ensure that the resulting dental appliance accommodates the unique spatial arrangement of the patient's temporalmandibular joint and maxilla (face-bow), and the interrelationship between maxilla and mandible (bite registration).

Figure 16:
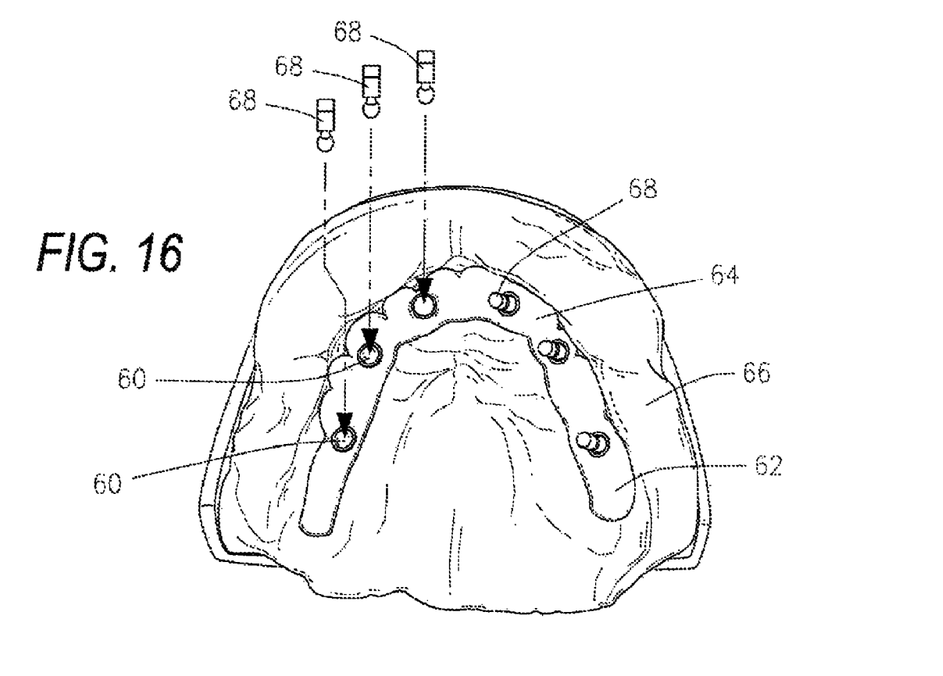

An impression is made of temporary teeth 64 in the usual fashion whereby a tray filled with impression material is placed into the patient's mouth. When the tray is removed from the patient's mouth, temporary teeth 64 remain embedded in the new impression 66 with gum side 62 and O-ring housings 60 facing outward (See FIG. 16). Implant analogs 68, such as MDL™ Laboratory Analogs (TM applied for, INTRA-LOCK INTERNATIONAL, INC., Boca Raton, Fla.)

are manually inserted into the exposed O-ring housings 60 in temporary teeth 64. The analogs will replicate mini-implants 28.

Figure 17:
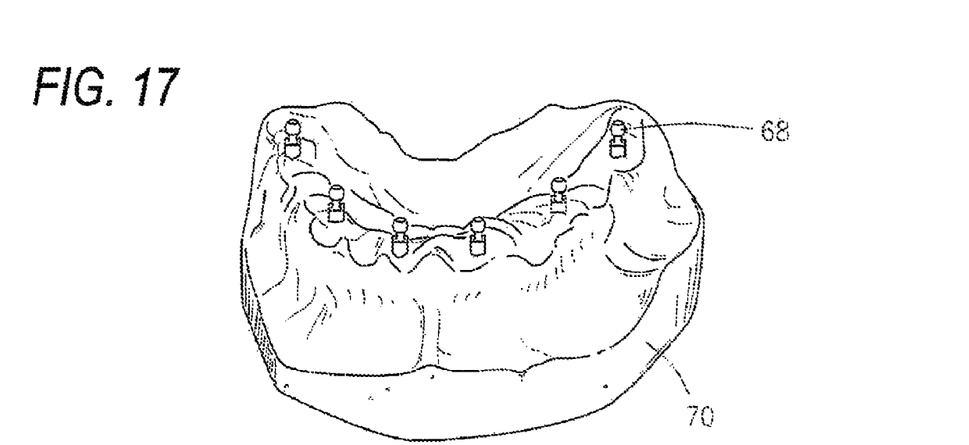

Impression 66 is poured up in dental stone using common techniques, thereby forming model 70 (See FIG. 17). Protruding from model 70 are implant analogs 68. Model 70 is then placed into the Biostar™ (not shown) and overlaid under heat and pressure with a single sheet of 0.1 mm Isofolan™ film 72 (SCHEU-DENTAL, Germany), thereby forming Isofolan™ mold 74 (See FIGS. 18 and 19). Persons skilled in the art will appreciate that heat, pressure and time settings for the Biostar™ and Isofolan™ film should be consistent with the manufacturer's instructions for each. Isofolan™ mold 74 comprises Isofolan™ film 72 and model 70 which is retained thereunder. The Isofolan™ film 72 facilitates the removal of materials, such as new prosthetic teeth, to be fabricated from model 70. As such, the Isofolan™ step is optional. Excess Isofolan™ film 72 may be trimmed from mold 74.

Figure 18:
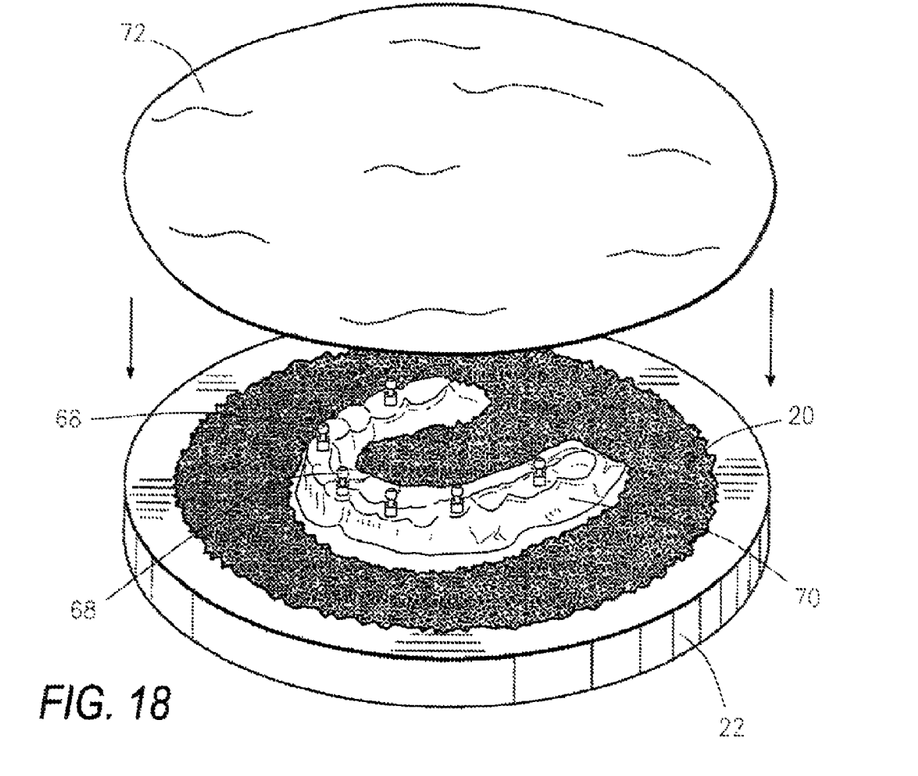
Figure 19:
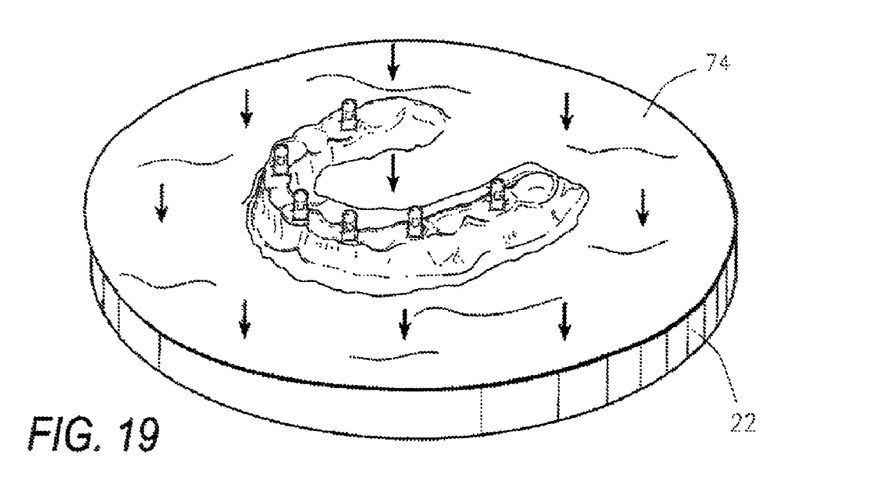

Isofolan™ mold 74 is then substituted for Isofolan™ mold 50 in the procedure first described above whereby prosthetic teeth are prepared. The principal difference is that Isofolan™ mold 74 has implant analogs 68 corresponding to the patient's implants while the structural equivalents of patient's implants are essentially concealed beneath ridge 42 on Isofolan™ mold 50. Persons skilled in the art will appreciate that in either instance, the resulting prosthetic teeth 56 will be adapted to the patient's mouth.

Alternatively, if implant analogs were not available or depending upon practitioner preference, new prosthetic teeth could be prepared with an appropriately-sized central channel or space into which the patient's mini-implants would easily fit. Upon placement in the patient's mouth, the remaining portions of the channel or space could be filled with fresh resin and cured.

Clinical Case Studies

The following are exemplary case studies. Except where expressly noted, each of the following patients underwent the treatment disclosed herein without further problems, complications or complaints:

Case Study #1

A. B., a 79-year-old female, presented with a history of ill-fitting dentures.

Case Study #2

B. G., a 74-year-old female, presented with an upper denture and a history of standard size implants and unsuccessful bone grails some 20 years earlier. Diagnosed with extensive maxillary bone loss. Following the treatment described herein, patient now exhibits radiographic evidence of new bone growth around implants and increased bone density.

Case Study #3

B. W., a 66-year-old female, presented edentulous with an O-ring retained lower denture. Chief complaint was shifting of denture during bite. Denies movement of new prosthodontics under increased biting pressures.

Case Study #4

B. B., a 67-year-old male, presented with upper denture complaining of movement.

Case Study #5

C. R., a 69-year-old female, presented with 5 natural upper teeth and 9 natural lower teeth, none of which were in apposition to prevent lower teeth from contacting palate. Contraindicated for traditional dentures.

Case Study #6

C. B., a 50-year-old female, presented with a history of 1 year of dentures and a prior diagnosis of contraindication for additional implants due to bone loss. Received an additional 19 implants without complication.

Case Study #7

C. G., a 60-year-old female, presented with a history 5 sets of dentures over 20 years and complaints of gum soreness and loosely fitting dentures. Standard implants and O-ring retained dentures were initially provided but the patient had persistent complaints of movement.

Case Study #8

E. S., a 56-year-old female, presented with severe bone atrophy secondary to 40 years of upper denture use. An O-ring retained denture was initially provided but the patient complained of loose fit.

Case Study #9

F. M., an 80-year-old male, presented edentulous with traditional dentures that were unsatisfactory due to an ultra-sensitive gag reflex. O-ring retained dentures were initially provided but were unsatisfactory.

Case Study #10

F. B., a 66-year-old male, presented with ill-fitting dentures and extensive bone loss. Implant failure incurred but successfully corrected.

Case Study #11

G. D., a 59-year-old female, presented with a history of 20 years use of dentures. Contraindicated for O-ring retained dentures due to bone loss. One complaint of numbness secondary to procedure, but declined implant removal in light of the benefits provided.

Case Study #12

J. A., a 59-year-old female, had a history of twenty years with an upper denture and presented with a number of loose lower teeth. Her diet was greatly restricted due to a poorly fitting lower denture.

Case Study #13

K. K., a 65-year-old female, had a history of several decades of full dentures. Patient was initially provided with O-ring retained denture. New bone growth was subsequently identified around implants.

Case Study #14

K. J., a 52-year-old female, presented with O-ring retained upper and lower dentures.

Case Study #15

L. A., a 65-year-old female, had a history of 50 years of wearing dentures. Patient initially provided O-ring retained dentures without satisfaction.

Case Study #16

L. H., a 62-year-old female, presented with missing teeth as well as fractured and infected natural dentition. Collapsed bite was restored with treatment disclosed herein.

Case Study #17

L. Y., a 60-year-old female, had a nine-year history of wearing dentures and complained of poor fitting.

Case Study #18

L. H., a 48-year-old female, presented status post upper teeth extraction and provision of an upper denture.

Case Study #19

M. D., a 59-year-old male, presented with healthy teeth numbering 6 lower anterior and 8 upper. Complained of chewing restricted to front teeth. Swelling of undetermined origin incurred but spontaneously resolved; asymptomatic since.

Case Study #20

M. W., an 81-year-old female, presented posteriorly edentulous and diminished front dentition due to aggressive brushing.

Case Study #21

M. M., a 58-year-old male, had a history of 40 years of denture use. Complained of instability of lower denture due to extensive bone loss. An O-ring retained denture was initially provided without satisfaction.

Case Study #22

M. B., an 80-year-old female, presented with rampant decay with several teeth having broken off at the gum line.

Case Study #23

P. Y., a 75-year-old female, had a history of 21 extracted teeth and presented with a one-year-old set of dentures. Patient complained of looseness at lower denture. Patient subsequently experienced right side paralysis secondary to a stroke, which would have rendered her previous dentures useless.

Case Study #24

R. R., a 65-year-old male, had a history of having lost some ⅓ of his natural teeth and several additional being crowned. At presentation, the patient's crowns were wearing down and his bite had collapsed.

Case Study #25

R. R., a 66-year-old female, presented with 5 upper teeth, four of which were infected.

Case Study #26

S. W., a 61-year-old female, complained of dissatisfaction with her adhesive dentures. A subsequent fracture in the new prosthodontic was easily repaired in the office.

Case Study #27

T. S., a 77-year-old female, presented with a full upper denture and a partial lower denture, the fit and appearance of which the patient was unhappy.

Case Study #28

V. U., a 73-year-old female, presented with a full upper denture and a lower partial denture and expressed a desire to have all of the removable appliances in her mouth removed.

Case Study #29

V. B., an 80-year-old male, presented with an implant-retained partial upper denture. Patient complained of poor fit.

Case Study #30

W. H., a 72-year-old female, presented with upper and lower O-ring retained dentures. Patient complained of inability to remove and replace dentures due to vision limitations. Subsequently reported that she had eaten corn-on-the-cob for the first time since age 25.

What is claimed is:

1. A method for preparing and seating prosthetic teeth, comprising the steps of:
    (1) making a first impression of the patient's mouth wherein said mouth does not contain any removable prosthetics;
    (2) by use of said first impression making a first model that replicates said patient's mouth;
    (3) preparing a denture setup on said first model;
    (4) making a second impression of said denture setup on said first model;
    (5) by use of said second impression making a second model that replicates said denture setup on said first model;
    (6) preparing a mold of said second model;
    (7) building a continuous structure in said patient's mouth wherein said structure connects two or more features selected from the group consisting of natural teeth and dental implants;
    (8) making a third impression of said patient's mouth including said structure;
    (9) by use of said third impression making a third model that replicates said patient's mouth including said structure;
    (10) preparing prosthetic teeth by filling said mold with a first moldable, dental restorative material and placing said mold filled with said moldable, dental restorative material onto said third model;
    (11) removing said prosthetic teeth from said mold; and
    (12) seating said prosthetic teeth in the mouth of said patient.

2. The method of claim 1 wherein the vertical and centric bite of the patient are registered before said denture setup is prepared, and wherein said denture setup is prepared to spatially conform to said vertical and centric bite of said patient.

3. The method of claim 1 wherein said denture setup further comprises reference teeth and is prepared using a method selected from the group consisting of selecting said reference teeth from a kit or library, modeling said reference teeth after the patient's existing dentition, and modeling said reference teeth after the patient's existing prosthesis.

4. The method of claim 1 further comprising the steps of, prior to step (7), identifying and assessing any existing natural teeth and existing dental implants of said patient.

5. The method of claim 4 further comprising the step of prior to step (7) extracting one or more of said patient's existing natural teeth.

6. The method of claim 4 further comprising the step of surgically placing one or more new implants in said patient's jaw, wherein the quantity of said new implants is medically appropriate.

7. The method of claim 6 wherein said new implants are mini-implants.

8. The method of claim 6 further including the step of performing one or more computed tomography scans.

9. The method of claim 8 wherein at least one said computed tomography scan is performed prior to said surgically placing of said new implants to determine bone depth, size and shape of maxillary sinuses and the location of nerves.

10. The method of claim 8 wherein at least one said computed tomography scan is performed subsequent to said surgically placing of said new implants to verify placement.

11. The method of claim 6 further including the step of performing sinus elevation prior to said surgically placing of said new implants.

12. The method of claim 1 wherein said mold is prepared by overlaying said second model with a first film and applying heat and pressure thereby causing said first film to conform to said second model.

13. The method of claim 12 wherein said heat and pressure are applied using a positive pressure device.

14. The method of claim 1 further including the step, between steps (9) and (10), of preparing a second mold of said third model, wherein said second mold is prepared by overlaying said third model with a second film and applying heat and pressure thereby causing said second film to conform to said third model, and further wherein said second mold is not removed from said third model.

15. The method of claim 14 wherein said heat and pressure are applied using a positive pressure device.

16. The method of claim 1 wherein said structure is built manually using a second moldable, dental restorative material.

17. The method of claim 16 wherein said second moldable, dental restorative material and said first moldable, dental restorative material are the same.

18. The method of claim 1 wherein said first moldable, dental restorative material is any moldable, dental restorative material that may cure or be cured in said mold.

19. The method of claim 1 wherein said first moldable, dental restorative material is selected from the group consisting of composite resins and acrylics.

20. The method of claim 19 wherein said first moldable, dental restorative material is a composite resin selected from the group consisting of hybrid composites, nanohybrid composites, micro-filled composites, and flowable composites.

21. The method of claim 20 wherein said first moldable, dental restorative material is a light curable, micro-filled composite resin.

22. The method of claim 21 further comprising the step of subjecting said mold filled with said first moldable, dental restorative material to a light source.

23. The method of claim 22 wherein said light source is a handheld LED curing light.

24. The method of claim 23 wherein said handheld LED curing light emits light in the blue visible spectrum.

25. The method of claim 1 wherein step (12) further comprises the steps of applying fresh first moldable, dental restorative material to said prosthetic teeth and placing said prosthetic teeth on said structure in said patient's mouth.

26. The method of claim 25 wherein said first moldable, dental restorative material is a light curable, micro-tilled composite resin.

27. The method of claim 1 further comprising the step of subjecting said prosthetic teeth to a light source.

28. The method of claim 27 wherein said light source is a handheld LED curing light.

29. The method of claim 28 wherein said handheld LED curing light emits light in the blue visible spectrum.

30. The method of claim 1 wherein said prosthetic teeth comprise a full arch.

31. The method of claim 1 wherein said prosthetic teeth comprise more than one tooth but fewer than a full arch.

32. A method for preparing and seating prosthetic teeth, comprising the steps of:

(1) making a first impression of the patient's mouth wherein said mouth does not contain any removable prosthetics;

(2) by use of said first impression making a first model that replicates said patient's mouth;

(3) preparing a denture setup on said first model;

(4) making a second impression of said denture setup on said first model;

(5) by use of said second impression making a second model that replicates said denture setup on said first model:

(6) preparing a mold of said second model;

(7) identifying and assessing any existing natural teeth and existing dental implants of said patient;

(8) performing one or more computed tomography scans;

(9) Surgically placing one or more new dental implants in said patient's jaw;

(10) building a continuous structure in said patient's mouth wherein said structure is constructed using a first moldable, dental restorative material and wherein said structure connects two or more features selected from the group consisting of natural teeth, said existing dental implants, and said new dental implants;

(11) making a third impression of said patient's mouth including said structure;

(12) by use of said third impression making a third model that replicates said patient's mouth including said structure;

(13) preparing prosthetic teeth by filling said mold with a second moldable, dental restorative material and placing said mold filled with said moldable, dental restorative material onto said third model;

(14) removing said prosthetic teeth from said mold; and (15) seating said prosthetic teeth in the mouth of said patient.

33. A method for preparing and seating prosthetic teeth, comprising the steps of:

(1) making a first impression of the patient's mouth wherein said mouth has at least one dental implant but does not contain any removable prosthetics;

(2) by use of said first impression making a first model that replicates said patient's mouth;

(3) preparing a denture setup on said first model;

(4) making a second impression of said denture setup on said first model;

(5) by use of said second impression making a second model that replicates said denture setup on said first model;

(6) preparing a mold of said second model;

(7) placing housings onto each of said patient's dental implants, wherein each of said housings contains an o-ring and is frictionally secured to each said dental implant by way of said o-ring;

(8) preparing temporary teeth by filling said mold with a first moldable, dental restorative material;

(9) adapting the gum side of said temporary teeth to receive said housings upon being placed in said patient's mouth, applying fresh said first moldable, dental restorative material to said gum side of said temporary teeth, and seating said temporary teeth in said patient's mouth;

(10) making a third impression of said temporary teeth in said patient's mouth, wherein upon removal of said third impression from said patient's mouth, said temporary teeth remain embedded in said third impression such that said gum side and said housings are visible;

(11) inserting implant analogs into said housings in said temporary teeth;

(12) by use of said third impression containing said temporary teeth, making a third model from which said temporary teeth are removable, and wherein said third model replicates said patient's gum line such that said implant analogs remain embedded in said third model and are adapted to receive said temporary teeth;

(13) preparing prosthetic teeth by filling said mold with a second moldable, dental restorative material and placing said mold filled with said second moldable, dental restorative material onto said third model;

(14) removing said prosthetic teeth from said mold; and (15) seating said prosthetic teeth in the mouth of said patient.

34. The method of claim 33 wherein said first moldable, dental restorative material is methyl-methacryate and wherein said second moldable, dental restorative material is a light curable, micro-filled composite resin.

* * * * *